United States Patent [19]

Etschenberg et al.

[11] 4,276,288

[45] Jun. 30, 1981

[54] DEHYDROOLIGOPEPTIDES, THEIR PRODUCTION AND THEIR MEDICINAL USE

[75] Inventors: Eugen Etschenberg; Wolfgang Opitz; Siegfried Raddatz, all of Cologne, Fed. Rep. of Germany

[73] Assignee: Troponwerke GmbH & Co., KG, Cologne, Fed. Rep. of Germany

[21] Appl. No.: 82,451

[22] Filed: Oct. 9, 1979

Related U.S. Application Data

[63] Continuation-in-part of Ser. No. 863,208, Dec. 22, 1977.

[30] Foreign Application Priority Data

Dec. 28, 1976 [DE] Fed. Rep. of Germany ....... 2659114
Oct. 11, 1977 [DE] Fed. Rep. of Germany ....... 2745584

[51] Int. Cl.$^3$ .................... A61K 37/00; C07C 103/52
[52] U.S. Cl. .............................. 424/177; 260/112.5 R
[58] Field of Search .................. 424/177; 260/112.5 R

[56] References Cited

PUBLICATIONS

Rich, et al., J.C.S. (1974) 897–898.
Riordan, et al., Tetrahedron Letter, No. 16, (1976), 1247–1250.
Bodansky, et al., Chem. Abstr. 72, (1970) 83007t.
Weiner, et al., J.A.C.S. 88, (1966) 3851–3859.
Doherty, et al., J. Biol. Chem. 147, (1943).
Benoitan, et al., J. Chem. Soc. (1964) 824–836.
Patchornik, et al., J.A.C.S. 86, 1860–1861.

*Primary Examiner*—Delbert R. Phillips
*Attorney, Agent, or Firm*—Sprung, Felfe, Horn, Lynch & Kramer

[57] ABSTRACT

New dehydrooligopepetides which bear, as one terminal substituent, an optionally substituted alkyl or alkenyl, optionally substituted aryl, optionally substituted heterocyclic radical, optionally substituted aralkyl or aralkenyl or a carbamoyl group and as the other terminal substituent a hydroxyl or amino, an optionally substituted alkylamino, optionally substituted arylamino, optionally substituted aralkylamino, an optionally substituted nitrogen-containing heterocyclic radical with five or six ring members optionally containing a further heteroatom, optionally substituted aralkoxy, optionally substituted alkoxy, optionally substituted aryloxy, optionally substituted alkylthio group or optionally substituted hydrazine demonstrate histolytic and tumor-resolving activity. The compounds are prepared by either hydrolyzing or aminolyzing the corresponding 2,4-disubstituted 5(4H)-oxazolones.

21 Claims, No Drawings

DEHYDROOLIGOPEPTIDES, THEIR PRODUCTION AND THEIR MEDICINAL USE

This is a continuation-in-part of application Ser. No. 863,208 filed Dec. 22, 1977.

The present invention relates to certain new dehydrooligopeptides, to processes for their production and to their use as tumour-resolving and/or histolytic acting agents.

It is known that a tumour-resolving and histolytic action can be achieved with substances of the most diverse nature; however, the general toxicity of such compounds is usually so high that practical treatment regimens which can be easily manipulated therapeutically and which do not harm the patients even further, scarcely exist.

Existing commercial products for use for corresponding indications are cytostatic agents, and cyclophosphamide may be mentioned here as an example.

All the agents used hitherto exhibit an extremely high general toxicity. This is frequently so pronounced that it becomes necessary to interrupt therapy, and thus the tumour diseases often end fatally.

The action of cyclophosphamide may be mentioned here as an example of the generally toxic action, Thus, M. H. N. TATTERSALL and J. S. TOBIAS report in The Lancet 1976/II, No. 7,994, page 1,071: "in the case of many anti-cancer agents, twice the dose which kills 10% of the animals ($LD_{10}$) is fatal for 90% of the animals ($LD_{90}$). FREI and FREIREICH (Advances in Chemotherapy 2 (1965), 269) were able to demonstrate the significance of using agents such as cyclophosphamide in dosages which approached the toxicity rate ($LD_{10}$). The decisive characteristic of these experiments was the exponential increase observed in cell destruction with a low (arithmetic) increase in dose. The $LD_{10}$ dosage of cyclophosphamide destroyed 99.999% of the tumour cells, but one eighth of this dose (which was far less toxic) destroyed only 90% of the tumour cells and was therefore less active clinically by 5 log.

This observation is the reason for the generally widely held view that chemotherapy of cancer is only effective when it is generally toxic."

The use of dehydrooligopeptides as medicaments has not yet hitherto been disclosed.

It has been found that the new compounds which are dehydrooligopeptides of the following general formula or their salts

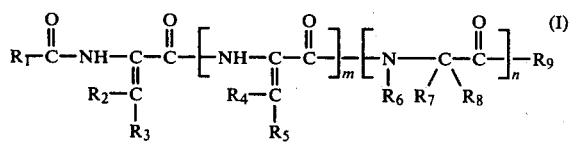

in which
$R_1$ is optionally substituted alkyl or alkenyl, optionally substituted aryl, an optionally substituted heterocyclic radical, optionally substituted aralkyl or aralkenyl or a carbamoyl group,
$R_2$ is a hydrogen atom or a lower alkyl group,
$R_3$ is an optionally substituted heterocyclic radical, optionally substituted aryl, optionally substituted aralkenyl or aralkyl, ethyl or cycloalkyl, or
$R_2$ and $R_3$, together with the carbon atom to which they are attached, represent a cyclopentylidene, cyclohexylidene, cyclopentenylidene or cyclohexenylidene group,
$R_4$ is a hydrogen atom, methyl or ethyl,
$R_5$ is a substituted phenyl group, optionally substituted aralkenyl or an optionally substituted heterocyclic radical,
$R_6$ is a hydrogen atom or alkyl, or
$R_6$ and $R_7$ together represent a divalent alkylene chain having three or four carbon atoms, or
when $R_6$ is a hydrogen atom or alkyl, $R_7$ is a substituted benzyl group or hydroxy-methyl, methylthioethyl, carbamoylethyl or carboxyethyl, and $R_8$ is hydrogen, or
$R_7$ and $R_8$ together represent a divalent alkylene chain having four or five carbon atoms,
$R_9$ is hydroxyl or amino, optionally substituted alkylamino, optionally substituted arylamino, optionally substituted aralkylamino, an optionally substituted aralkylamino, an optionally substituted nitrogen-containing heterocyclic radical with five or six ring members optionally containing a further heteroatom, optionally substituted aralkoxy, optionally substituted alkoxy, optionally substituted aryloxy, optionally substituted alkylthio group or optionally substituted hydrazino and
m and n are the same or different and each represents the number 0 or the number 1, provided that both m and n may not simultaneously be 0,
provided that
when $R_1$ is methyl $R_2$ is hydrogen, $R_3$ is phenyl, m represents 0, $R_6$ is hydrogen, $R_9$ is hydroxyl, $R_8$ is hydrogen and n is 1, $R_7$ may not represent the 4-hydroxy-benzyl radical, possess a surprisingly highly pronounced histolytic and tumour-resolving action in transplanted tumours.

The dehydrooligopeptides according to the invention influence, in an outstanding manner, biological tissues which prevent or interfere with the course of normal biological functions.

Substances which are closely related chemically to the dehydrooligopeptides and which have a comparable action have not hitherto been disclosed.

Among the new salts of the invention those salts that are pharmaceutically acceptable are particularly important and are preferred.

The new free acid compounds of the general formula (I) and their salts can be interconverted in any suitable manner; methods for such interconversion are known in the art.

When in the general formula (I) m represents 0 and n represents 1, the following type of structure derived from the general formula (I) results:

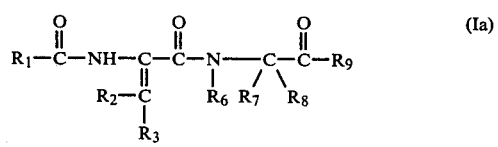

wherein, in the formula Ia the radicals $R_1$, $R_2$, $R_3$, $R_6$, $R_7$, $R_8$ and $R_9$ have the above mentioned meaning.

In preferred compounds of formula (Ia), $R_9$ is hydroxyl or amino, optionally substituted alkylamino, optionally substituted arylamino, optionally substituted aralkylamino, an optionally substituted nitrogen containing heterocyclic radical with five or six ring members optionally containing a further hetero-atom, optionally substituted aralkoxy, optionally substituted alkoxy or optionally substituted aryloxy.

When in the general formula (I) m represents 1 and n represents 0, the following type of structure derived from the general formula (I) results:

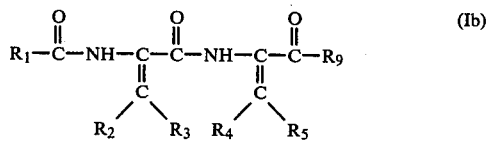

wherein, in the formula (Ib), the radicals $R_1$, $R_2$, $R_3$, $R_4$, $R_5$ and $R_9$ have the above mentioned meaning.

In preferred compounds of formula (Ib) $R_1$ is optionally substituted alkyl, optionally substituted aryl, an optionally substituted heterocyclic radical or optionally substituted aralkyl or aralkenyl, and $R_9$ is hydroxyl or amino, optionally substituted alkylamino, optionally substituted arylamino, optionally substituted aralkylamino, an optionally substituted nitrogen containing heterocyclic radical with five or six ring members optionally containing a further hetero-atom, optionally substituted aralkoxy, optionally substituted alkoxy or optionally substituted aryloxy.

When in the general formula (I) both m and n represent 1, the following type of structure, which can be derived from the general formula (I), results:

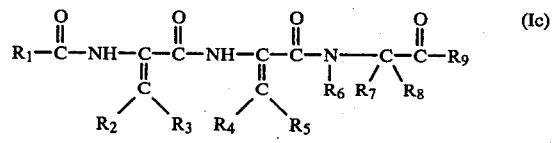

wherein the radicals $R_1$ to $R_9$ have the above mentioned meaning.

Particularly preferred compounds are of the derived structure types (Ia) and (Ib), and in particular of structure type (Ia).

Particularly preferred compounds of structure type (Ia) are the compounds of the following formula:

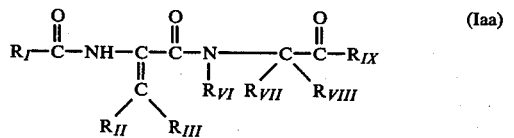

in which
$R_I$ is alkyl having from one to four carbon atoms or phenyl or styryl,
$R_{II}$ is a hydrogen atom,
$R_{III}$ is thienyl, furyl, or cycloalkyl having five or six carbon atoms,
$R_{VI}$ is a hydrogen atom,
$R_{VII}$ is the 4-hydroxybenzyl radical, 4-nitrobenzyl radical or the 4-chlorobenzyl radical, the 2-methylmercaptoethyl radical or the carboxymethyl radical,
$R_{VIII}$ is a hydrogen atom and
$R_{IX}$ is hydroxyl or alkoxy having from one to four carbon atoms.

In the formulae I, Ia, Ib and Ic, the radicals $R_1$ to $R_9$ have the preferred meanings listed in the following text:

The optionally substituted alkyl group $R_1$ in the general formula I denotes a straight-chain or branched optionally substituted alkyl radical preferably having from one to six carbon atoms. Examples which may be mentioned are methyl, propyl, i-propyl, butyl, i-butyl, n-pentyl and i-pentyl. In each case the alkyl can be substituted by from one to three halogen atoms, preferably fluorine or chlorine atoms, alkoxy having from one to three carbon atoms, preferably methoxy, or a heterocyclic radical, preferably thienyl.

The optionally substituted aryl group $R_1$ preferably denotes phenyl or naphthyl, optionally substituted by from one to three halogen atoms, preferably chlorine or fluorine atoms, or by alkyl or alkoxy, each having preferably from one to three carbon atoms, hydroxyl, trifluoromethyl or nitro.

The optionally substituted heterocyclic radical $R_1$ preferably denotes a five-membered to seven-membered heterocyclic radical, optionally containing one or two nitrogen, oxygen or sulphur atoms. Examples which may be mentioned are pyridyl, thienyl, furyl, pyrrolyl, oxazolyl and imidazolyl, which can each be additionally substituted by one or two halogen atoms or alkyl or alkoxy groups, each preferably having from one to four carbon atoms.

The optionally substituted aralkyl or aralkenyl group $R_1$ preferably denotes an optionally substituted aralkyl or aralkenyl group having from eight to twelve carbon atoms, most preferably optionally substituted benzyl or styryl, optionally substituted by from one to three halogen atoms, in particular chlorine or fluorine atoms, alkyl or alkoxy having preferably from one to three carbon atoms, most preferably methyl and methoxy, hydroxyl, lower acyloxy, or halogenoalkyl most preferably trifluoromethyl.

A lower alkyl group $R_2$ or $R_4$ as used herein denotes an alkyl group having from one to four carbon atoms, most preferably methyl or ethyl.

The optionally substituted heterocyclic radical $R_3$ preferably denotes a saturated or unsaturated heterocyclic radical having from five to seven ring members, in which one or two hetero-atoms, such as, for example, nitrogen, oxygen and sulphur atoms, can be present. Examples which may be mentioned are pyrrolyl, thienyl, furyl, oxazolyl, thiazolyl, imidazolyl, piperidinyl, morpholinyl and pyridinyl, thienyl and furyl being particularly preferred. In each case the heterocyclic radical can be substituted by from one to three halogen atoms, preferably chlorine or fluorine atoms, by alkyl or alkoxy having most preferably one or two carbon atoms or, for example, by nitro.

The optionally substituted aryl group $R_3$ preferably denotes a phenyl or naphthyl group, which can be substituted, for example, by from one to three halogen atoms, preferably chlorine or fluorine atoms, by alkyl or alkoxy having from one to four carbon atoms, by hydroxyl or by nitro.

The optionally substituted aralkyl or aralkenyl group $R_3$ preferably denotes a phenyl-alkyl or -alkenyl group having from seven to ten carbon atoms. Examples which may be mentioned are benzyl, phenylethyl and styryl, optionally substituted by from one to three halogen atoms, alkyl or alkoxy having from one to four carbon atoms or by nitro.

The cycloalkyl radical $R_3$ denotes a cycloalkyl radical having preferably from four to six carbon atoms, such as, for example, the cyclobutyl, cyclopentyl or, in particular, the cyclohexyl radical, which can be substituted, for example, by one to two lower alkyl radicals with one to three carbon atoms.

The optionally substituted phenyl group $R_5$ means that the phenyl group can be substituted by from one to three halogen atoms, in particular chlorine or fluorine atoms, by from one to three alkyl or alkoxy groups having preferably from one to three carbon atoms or by nitro or dialkylamino groups, in particular dimethylamino groups.

The optionally substituted aralkenyl group $R_5$ denotes an aralkenyl group having preferably from eight to ten carbon atoms, in particular the styryl group, which can be substituted by from one to three halogen atoms, hydroxyl, nitro or alkyl or alkoxy having preferably from one to three carbon atoms.

The optionally substituted heterocyclic radical $R_5$ is an optionally substituted heterocyclic radical having from five to seven ring members and containing one or two nitrogen or oxygen or sulphur hetero atoms, optionally substituted by from one to three halogen atoms, hydroxyl, nitro or alkyl or alkoxy having preferably from one to three carbon atoms.

The substituted benzyl group $R_7$ is to be understood as being a benzyl group which can be substituted by one or two halogen atoms, in particular chlorine and fluorine atoms, or by hydroxyl, nitro, alkoxy or alkyl having preferably from one to three carbon atoms.

The optionally substituted alkylamino group $R_9$ denotes a straight-chain or branched saturated or unsaturated monoalkylamino or dialkylamino group having preferably from one to ten, in particular from one to six, carbon atoms. Examples which may be mentioned are the methylamino, dimethylamino, ethylamino, diethylamino, propylamino, isopropylamino, butylamino, pentylamino and hexylamino groups and the 1,1-dimethyl-2-propinylamino group.

The arylamino group $R_9$ denotes, most preferably, phenylamino or naphthylamino.

The aralkylamino group $R_9$ denotes most preferably benzylamino or phenethylamino.

The aryloxy group $R_9$ denotes, most preferably, phenloxy or naphthyloxy.

The alkoxy group $R_9$ preferably denotes methoxy, ethoxy, propoxy, isopropoxy, butoxy, isobutoxy, secondary butoxy, tertiary butoxy or pentoxy, in particular methoxy or ethoxy.

The aralkoxy group $R_9$ preferably means benzyloxy or phenethyloxy.

The nitrogen-containing heterocyclic radical having from five to seven ring members $R_9$ preferably denotes pyrrolidino, pyrryl, oxazolinyl, thiazolinyl, piperidino or morpholinyl most preferably morpholinyl.

The alkylamino, aralkylamino, alkoxy, aryloxy, aralkyloxy and arylamino groups and heterocyclic radicals designated as $R_9$ can be substituted, for example, by from one to three halogen atoms, hydroxyl groups, nitro groups, amino groups or lower alkylamino or lower dialkylamino or alkyl or alkoxy groups having from one to four carbon atoms.

When $R_6$ together with $R_7$ represents a divalent alkylene group having two or three carbon atoms, this means that a pyrrolidine or a piperidine ring is formed in the compound of formula I.

When $R_7$ together with $R_8$ represents a divalent alkylene group having four or five carbon atoms, this means that a cyclohexyl or, preferably, a cyclopentyl ring is formed in the compound of formula I.

Moreover, it has been found that the compounds, according to the invention, of the general formula (I) in which $R_1$ to $R_9$, m and n have the above mentioned meaning, are obtained when the corresponding 2,4-disubstituted 5(4H)-oxazolones are either hydrolysed or aminolysed in accordance with the general reaction equation:

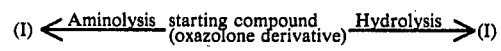

In a further aspect of the present invention provides a process for the production of a compound according to the invention in which:

(a) (hydrolysis) when said compound is a compound of the formula (I) in which the radicals $R_1$, $R_2$, $R_3$, $R_4$ and $R_5$ have the same meaning as defined hereinbefore, $R_9$ is hydroxyl, n represents 0 and m represents 1, an oxazolone of the general formula

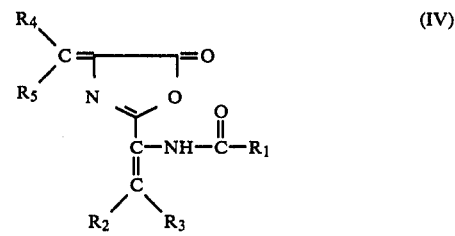

in which $R_1$, $R_2$, $R_3$, $R_4$ and $R_5$ have the same meaning as defined hereinbefore in the formula I, is hydrolysed so as to yield said compound of the formula I, (b) (aminolysis) when said compound is a compound of the general formula (I) in which $R_1$, $R_2$, $R_3$, $R_6$, $R_7$, $R_8$ and $R_9$ have the same meaning as defined hereinbefore, n represents 1 and m represents 0, an oxazolone of the general formula

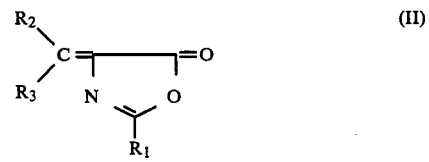

in which $R_1$, $R_2$ and $R_3$ have the same meaning as defined hereinbefore in formula I is reacted with a compound of the general formula

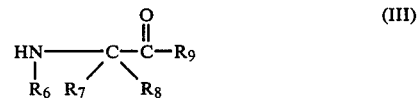

in which $R_6$, $R_7$, $R_8$ and $R_9$ have the same meaning as defined hereinbefore in formula I so as to yield said compound of formula I, or (c) (aminolysis) when said compound is a compound of the general formula (I) in which $R_1$, $R_2$, $R_3$, $R_4$, $R_5$, $R_6$, $R_7$, $R_8$ and $R_9$ have the same meaning as defined hereinbefore and both m and n represent 1, an oxazolone of the general formula

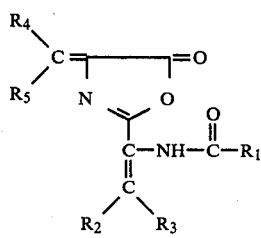

(IV)

in which $R_1$, $R_2$, $R_3$, $R_4$ and $R_5$ have the same meaning as defined hereinbefore in formula (I) is reacted with a compound of the general formula

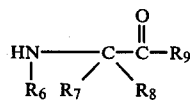

(III)

in which $R_6$, $R_7$, $R_8$ and $R_9$ have the same meaning as defined hereinbefore in formula (I), so as to yield said compound of formula (I), and the resulting compound of formula (I) or salt thereof, is optionally converted into a salt or the corresponding compound of formula (I), respectively.

The compounds of the general formula IV may be hydrolysed by stirring it or allowing it to stand in the presence of diluent(s).

Both polar aprotic and protic organic solvents can be used as diluents. Examples of polar aprotic diluents which may be mentioned are ketones, such as, for example, acetone, methyl ethyl ketone and diethyl ketone, and cyclic ethers (tetrahydrofurane and dioxane). Acetone and tetrahydrofurane are particularly preferred.

Examples of polar protic diluents which may be mentioned are water and lower alcohols, such as methanol, ethanol, propanol or isopropanol.

The reaction may appropriately be carried out in the presence of acid or basic catalysts.

Acid catalysts which can be employed are strong mineral acids, such as hydrochloric acid or sulphuric acid, or strong organic acids, such as benzenesulphonic acid or toluene-sulphonic acid.

Inorganic bases, such as sodium hydroxide or potassium hydroxide, and strong organic bases, such as triethylamine, have proved to be suitable basic catalysts. Sodium hydroxide and potassium hydroxide are particularly preferred.

The reaction temperatures can be varied within a wide range. In general, the reaction is carried out at from 0° to 70° C., preferably from 10° to 30° C.

If acid catalysts are used, small amounts of the catalyst are sufficient to achieve a satisfactory hydrolysis; if basic catalysts are used, it has proved desirable to employ 1 mol of base per 1 mol of oxazolone.

The reaction time varies with other conditions though in general it is between 15 minutes and 180 minutes, and usually is from 30 to 120 minutes. The reaction solution is usually worked up by acidifying with dilute aqueous mineral acids or relatively strong organic acids and evaporating off the organic diluent, whereupon the reaction product usually precipitates and is then recrystallised from the organic solvents customarily used, such as, for example, dilute alcohols and ethyl acetate. The yields are in general good and are usually over 70%.

The preparation of the compounds of the general formula (I) by aminolysis of (II) or (IV) in the presence of (III) is usually carried out by stirring the reactants together in diluents.

Suitable diluents are those organic liquids which are polar aprotic liquids and are miscible with water. Examples which may be mentioned are acetone, methyl ethyl ketone, diethyl ketone, alcohols and cyclic ethers, such as dioxane and tetrahydrofurane. Acetone and tetrahydrofurane have proved to be particularly suitable.

The process according to the invention is preferably carried out in the presence of basic catalysts. Sodium hydroxide has proved to be particularly suitable.

If free aminoacid as a reactant is used in the condensation with the oxazolone, 1 mol of aminoacid and 1 mol of sodium hydroxide are preferably employed per 1 mol of oxazolone. The reaction temperatures can be varied within a certain range; in general, the reaction is carried out at from 0° to 80° C., preferably at from 10° to 30° C., since at higher temperatures side reactions proceed and the yield is less.

The reaction time varies and may be between 30 minutes and several days, though usually it is from one to three hours. The reaction solution may be worked up by filtering and acidifying the filtrate with dilute mineral acids. It is particularly preferable to use 1 mol of mineral acid per 1 mol of sodium hydroxide employed. The reaction products are usually isolated by evaporating off the organic diluent in vacuo, whereupon the reaction product precipitates and is recrystallised from etheral organic solvents, such as dilute alcohols or acetone.

When carrying out the process according to the invention using derivatives of aminoacids, for example aminoacid esters or amides, as reactants with the oxazolones, it is appropriate to carry out the reaction without basic catalysts, since hydrolytic splittings of the ester bonds or amide bonds could take place as side reactions.

In some cases it has proved appropriate, for reasons of purity and yield, to use, instead of a free aminoacid of the general formula (III) ($R_9$=OH), the corresponding ester in the condensation and subsequently to split off the ester grouping hydrolytically in a manner which is in itself known.

If the reaction times are extremely long, partial racemisation cannot be excluded, as can be seen from some of the optical rotation values quoted in the examples.

The compounds of the invention can exist both in the form of a racemate and in the form of the isolated optical isomers with a definite absolute configuration. In addition, cis/trans isomers can be obtained in the syntheses, for example of N-benzoyldehydro-phenylalanyl-leucine methyl ester. In some cases, for example in the case of N-acetyldehydro-3-(2-thienyl)alanyl-L-tyrosine, only one of the isomers is preferentially formed, as may be demonostrated by $^{13}$C-NMR spectroscopy.

Some of the starting compounds of formulae (II) and (IV), for the preparation of the compounds of the general formula (I) according to the invention, that is to say the corresponding 2,4-disubstituted 5(4H)-oxazolones, are known from the literature. If they are not known, they can be prepared by the methods described in the literature for the preparation of compounds of analogous structure. The reaction of acetylglycine with benzaldehyde may be described here as an example. The reaction takes place according to to the equation

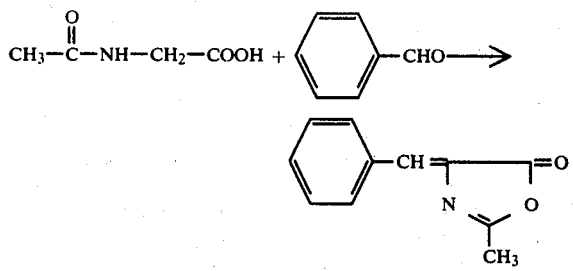

The reaction is carried out by mixing the two components in an equimolar ratio in the presence of a condensing agent, usually acetic anhydride, which at the same time serves as the solvent, and a basic component, such as sodium acetate. After standing for several hours, the mixture is worked up by diluting with water and recrystallising the 4-benzylidene-2-methyl-5(4H)-oxazolone, which was precipitated, from ethyl acetate/petroleum ether.

Further examples of starting compounds which can be prepared analogously to the above equation follow.

5(4H)-Oxazolone starting materials of the formula (II) which may be mentioned are: 2-methyl-4-(2-thenylidene)-5(4H)-oxazolone, melting point 130°–132° C.; 2-methyl-4-(2-naphthylmethylene)-5(4H)-oxazolone, melting point 132°–133° C.; 4-cyclohexylmethylene-2-phenyl-5(4H)-oxazolone, melting point 114° C.; 4-benzylidene-2-trifluoromethyl-5(4H)-oxazolone, melting point 98°–100° C.; 4-(1-methylpropylidene)-2-phenyl-5(4H)-oxazolone, oil; 2-phenyl-4-(2-thenylidene)-5(4H)-oxazolone, melting point 178° C.; 2-(3-pyridyl)-4-(2-thenylidene)-5(4H)-oxazolone, melting point 193° C.; 4-(1-methyl-3-phenyl-2-propylidene)-2-phenyl-5(4H)-oxazolone, melting point 125° C.; 4-thenylidene-2-(3-trifluoromethylphenyl)-5(4H)-oxazolone, melting point 156° C.; 4-(2-cyclohexenylidene)-2-phenyl-5(4H)-oxazolone, melting point 100° C.; 4-(1-methyl-2-phenylethylidene)-2-phenyl-5(4H)-oxazolone, melting point 63° C.; 4-(α-methylbenzylidene)-2-phenyl-5(4H)-oxazolone, melting point 105.5° C.; 4-cyclohexylidene-2-phenyl-5(4H)-oxazolone, melting point 136° C.; 2-benzyl-4-(2-thenylidene)-5(4H)-oxazolone, melting point 97°–100° C.; 2-cinnamenyl-4-benzylidene-5(4H)-oxazolone, melting point 131°–135° C.; 2-phenyl-4-(α-methyl-2-thenylidene)-5(4H)-oxazlone, melting point 154° C.; 2-methyl-4-benzylidene-5(4H)-oxazolone, melting point 148°–150° C.; 2-methyl-4-(3-nitro-4-acetoxy-benzylidene)-5(4H)-oxazolone, melting point 164° C.; 2-methyl-4-(4-methylbenzylidene)-5(4H)-oxazolone, crude product; 2-methyl-4-(2-furfurylidene)-5(4H)-oxazolone, crude product (product from the literature); 2-methyl-4-(3-phenyl-2-propenylidene)-5(4H)-oxazolone, crude product; 2-(1-propenyl)-4-(2-thenylidene)-5(4H)-oxazolone, melting point 131°–2° C.; 2-[2-(3,4,5-trimethoxyphenyl)vinyl]-4-(2-thenylidene)-5(4)-oxazolone, melting point 163° C.; 2-methyl-4-(5-nitrothenylidene-2)-5(4H)oxazolone, product from the literature; 2-(2-thienyl)-4-(2-thenylidene)-5(4H)oxazolone, melting point 174° C.; 2-phenyl-4-(4-pyridylmethylene)-5(4H)oxazolone, melting point 237°–239° C.; 2-(4-nitrophenyl)-4-(2-thenylidene)-5(4H)oxazolone, melting point 182°–183° C.; 2-(2-thienylmethyl)-4-(2-thenylidene)-5(4H)oxazolone, melting point 104° C.; and 2-phenyl-4-(1-methylpropylidene)-5(4H)oxazolone, product from the literature.

5(4H)Oxazolone starting materials of the formula IV which may be mentioned are: 2-(1-acetamido-2-phenylvinyl)-4-(4-dimethylaminobenzylidene)-5(4H)-oxazolone, melting point 253°–254° C.; 2-(1-acetamido-2-phenyl-vinyl)-4-(4-hydroxybenzylidene)-5(4H)-oxazolone, melting point 187°–189° C.; 2-(1-acetamido-2-phenylvinyl)-4-(4-fluorobenzylidene)-5(4H)-oxazolone, crude product; 2-(1-acetamido-2-phenylvinyl)-4-(4-nitrobenzylidene)-5(4H)-oxazolone, melting point 235°–241° C.; 2-(1-acetamido-2-phenylvinyl)-4-(4-chlorobenzylidene)-5(4H)-oxazolone, melting point 216°–219° C.; 2-[1-acetamido-2-(2-thienyl)vinyl]-4-(2-thenylidene)-5(4H)-oxazolone, melting point 229° C.; 2-[1-acetamido-2-phenylvinyl]-4-(5-methyl-2-thenylidene)-5(4H)oxazolone, melting point 185°–187° C.; 2-[1-acetamido-2-(2-thienyl)vinyl]-4-(α-methyl-2-thenylidene)-5(4H)-oxazolone, melting point 217° C. and 2-(1-acetamido-2-phenyl-vinyl)-4-(3-chlorobenzylidene)-5(4H)-oxazolone, melting point 207°–208° C.

The compounds of the formula III (preferably amino-acids and their amides or esters) used as starting compounds are known from the literature.

Examples which may be mentioned are: glycine, alanine, leucine, proline, phenylalanine, tyrosine, serine, threonine, cysteine, methionine, glutamine, aspartic acid, glutamic acid, 1-aminocyclopentanecarboxylic acid, tyrosine N-methylamide, fluoroalanine, p-nitrophenylalanine, tyrosine tert.-butyl ester, tyrosine methyl ester, tyrosine amide, benzylamide and hexylamide and tyrosine ethyl ester.

If the aminoacids and their amides or esters used as starting compounds are not known, they can be prepared by processes which are in themselves known for preparing compounds of analogous structure.

Examples of the compounds according to the invention which may be mentioned are: N-acetyl-DL-phenylalanyldehydro-(3-chlorophenyl)alanine, N-acetyldehydrophenylalanyl)-D-proline, N-acetyldehydrophenylalanyl-D-tyrosine, N-acetyldehydrophenylalanyl-L-methionine, N-acetyldehydrophenylalanyl-L-aspartic acid, N-acetyldehydrophenylalanyl-L-glutamine, N-acetyldehydro-phenylalanyl-DL-3-fluoroalanine, N-acetyldehydrophenylalanyl-L-serine, N-acetyldehydrophenylalanyl-L-(p-nitrophenyl)-alanine, N-acetyldehydrophenylalanyl-DL-(p-chlorophenyl)alanine, N-trifluoroacetyldehydrophenylalanyl-L-tyrosine, N-acetyldehydro-(p-methylphenyl)alanyl-L-tyrosine N-benzoyl-2-cyclohexylidene-glycyl-L-tyrosine, N-benzoyl-2-(2-cyclohexyidene)-glycyl-L-tyrosine, N-acetyldehydro-3-(2-furyl)alanyl-L-tyrosine, N-acetyldehydro-3-cinnamenylalanyl-L-tyrosine, N-acetyldehydro-3-(2-naphthyl)alanyl-L-tyrosine, N-benzoyldehydro-3-cyclohexyl-alanyl-L-tyrosine, N-trifluoroacetyldehydrophenylalanyl-L-tyrosine tert.-butyl ester, N-benzoyldehydro-3-(2-thienyl) alanyl-L-proline, N-acetyldehydrophenylalanine (1-carboxyl-1-cyclopentyl)amide, N-acetyldehydro-3-(2-thienyl)alanyl-L-tyrosine, N-phenacetyldehydro-3-(2-thienyl)alanyl-L-tyrosine tert.-butyl ester, N-phenacetyldehydro-3-(2-thienyl)alanyl-L-tyrosine, N-benzoyldehydro-3-(2-thienyl)alanyl-L-tyrosine, N-benzoyldehydro-3-(2-thienyl)alanyl-L-(p-nitrophenyl)-alanine, N-nicotinoyldehydro-3-(2-thienyl)alanyl-L-tyrosine, N-(3-trifluoromethylbenzoyl)dehydro-3-(2-thienyl)alanyl-L-tyrosine, N-nicotinoyldehydro-3-(2-thienyl)alanyl-L-(p-nitrophenyl)alanine, N-benzoyl-3-methyl-3-(2- thienyl)dehydroalanyl-L-tyrosine, N-acetyldehydro-3-(2-thienyl)alanyl-D-tyrosine, N-benzoyldehydro-3-(2-thienyl)alanyl-L-tyrosine methyl ester, N-acetyldehydro-3-(2-thienyl)alanyl-L-tyrosine methyl ester, N-benzoyldehydro-3-(2-thienyl)alanyl-L-tyrosine amide, N-benzoyldehydro-3-(2-thienyl)alanyl-L-tyrosine N'-hexylamide, N-benzoyldehydro-3-(2-thienyl)alanyl-L-tyrosine N'-cyclohexylamide, N-benzoyldehydro-3-(2-thienyl)alanyl-L-tyrosine N',N'-dimethylamide, N-benzoyldehydro-3-(2-thienyl)alanyl-L-tryosine morpholide, N-acetyldehydrophenylalanyldehydro-(p-nitrophenyl)-alanine, N-acetyldehydrophenylalanyldehydro(p-fluorophenyl)-alanine, N-acetyldehydrophenylalanyldehydro-( 4-dimethylaminophenyl)alanine, N-acetyldehydrophenylalanyldehydro-(3-chlorophenyl)alanine, N-acetyldehydrophenylalanyldehydro-(3-chlorophenyl)-alanyl-L-tyrosine, N-acetyldehydrophenylalanyl-D-glutamic acid, N-benzoyldehydro-3-(2-thienyl) alanyl-L-tyrosine benzyl ester, N-benzoyldehydro-3-(2-thienyl)-L-tyrosine N'-benzylamide, and N-benzoyl-3-methyl-3-cinnamenyldehydroalanyl-L-tyrosine. Additional examples of compounds according to the invention which may be mentioned are: N-acetyldehydrophenylalanyl-3-(5-methyl-2-thienyl)-dehydroalanine, N-acetyldehydrophenylalanyl-3-(chlorophenyl)-dehydroalanine thiomethyl ester, N-acetyldehydro-3-(2-thienyl)-alanyldehydro-3-(2-thienyl)alanine, N-acetyldehydro-3-(2-thienyl)alanyldehydro-3-(4-nitrophenyl) alanine, N-(3,4,5-trimethoxycinnamoyl)-dehydro-3-(2-thienyl) alanyl-L-tyrosine, N-crotonyl-dehydro-3-(2-thienyl)alanyl-L-tyrosine, N-acetyldehydro-3-(5-nitro-2-thienyl)alanyl-L-tyrosine, N-(2-thenoyl)-dehydro-3-(2-thienyl)alanyl-L-tyrosine, N-acetyldehydro-3-(2-thienyl)alanyl-O-methyl-L-tyrosine, N-acetyldehydro-3-(2-thienyl)alanyl-L-glutamic acid, N-acetyldehydro-3-(2-thienyl)dehydroalanyl-L-tyrosine tert.-butyl ester, N-acetyldehydro-3-(2-thienyl) alanyl-3-(2-thienyl)dehydroalanyl-L-tyrosine benzyl ester, N-acetyldehydro-3-(2-thienyl)alanyl-3-(2-thienyl)dehydroalanyl-L-tyrosine methyl ester, N-acetyldehydro-3-(2-thienyl) alanyl-N-methyl-L-tyrosine methyl ester, N-acetyldehydro-3-(2-thienyl)alanyl-N-methyl-L-tyrosine, N-acetyldehydro-3-(3-nitro-4-hydroxyphenyl)alanyl-L-tyrosine tert.-butyl ester, N-acetyldehydro-3-(3-nitro-4-hydroxyphenyl)alanyl-L-tyrosine, N-benzoyldehydro-3-(4-pyridyl)alanyl-L-tyrosine methyl ester, N-benzoyldehydro-3-(4-pyridyl)alanyl-L-tyrosine, N-(4-nitrophenyl)acetyldehydro-3-(2-thienyl)alanyl-L-tyrosine, N-(4-nitrophenyl)acetyldehydro-3-(2-thienyl)alanyl-L-tyrosine methyl ester, N-acetyldehydro-3-(2-thienyl)alanyl-3-(2-thienyl)dehydroalanyl-L-tyrosine tert.-butyl ester, N-acetyldehydro-3-(2-thienyl)alanyl-3-(2-thienyl)dehydroalanyl-L-tyrosine, N-benzoyldehydroisoleucyl-L-tyrosine methyl ester, N-(2-thienyl)acetyldehydro-3-(2-thienyl)alanyl-L-tyrosine, N-(2-thienyl)acetyldehydro-3-(2-thienyl)alanyl-L-tyrosine tert.-butyl ester, N-(2-thienyl)acetyldehydro-3-(2-thienyl)alanyl-L-tyrosine benzyl ester, N-(2-thienyl)acetyldehydro-3-(2-thienyl)-alanyl-L-tyrosine methyl ester, the salt of N-acetyldehydro-3-(2-thienyl)alanyl-L-tyrosine with morpholine, with piperidine, with ethylenediamine, with triethanolamine, with DL-canavanine, with L-arginine and with L-lysine, N-acetyldehydro-3-(2-thienyl)alanyl-L-tyrosine 2-dimethylaminopropylamine, N-acetyldehydro-3-(2-thienyl)alanyl-L-tyrosine amide, N-acetyldehydro-3-(2-thienyl)alanyl-L-tyrosine methylamide, N-acetyldehydro-3-(2-thienyl)alanyl-L-tyrosine hydrazide, N-benzoyldehydro-3-(2-thienyl)alanyl-L-tyrosine 6-aminohexanylamide, N-benzoyldehydro-3-(2-thienyl)alanyl-L-tyrosine 4-aminobutylamide, N-benzoyldehydro-3-(2-thienyl)alanyl-L-tyrosine hydrazide, N-acetyldehydrophenylalanyl-3-(2-thienyl)dehydroalanine methylamide and N-acetyldehydro-3-(2-thienyl)alanyl-3-methyl-3-(2-thienyl)-dehydroalanine hexylamide.

On local administration, the active compounds according to the invention have a tumour-resolving and histolytic action in transplanted tumors which depends on the dosage used. By local administration there are to be understood herein as being included in particular, the following types of administration: subcutaneous, intracutaneous, intratumoral and peritumoral administration.

Necroses usually occur in the immediate region of the point of administration, but occasionally also at a distance therefrom (Lymphogenic). If the necrotic region breaks open, it is free from putrid material even for a relatively long period, although in the case of experimental animals feed, faeces, sawdust and other material come into contact with the open wound.

However, the transplanted tumor tissue can also be broken down whilst the external skin remains completely intact.

The activity of the third component of the immunohaemolytic complement system is considerably decreased.

The necrotic tissue is sharply divided from the surrounding heathly tissue; it appears macroscopically and microscopically as if it were "stamped out".

The general behaviour of the experimental animals is not influenced by the size of the necrosis. There is no poisoning of the entire organism.

In the acute test for intravenous injection in rats, the $LD_{50}$ of the compounds according to the invention is of the order of size of 300 mg/kg.

A daily injection of 80 mg/kg in rabbits over a period of 27 days was tolerated completely without reaction.

As has been mentioned above, the present invention also includes the use of the active compounds according to the invention for the treatment of those tissues in the field of medicine which prevent and interfere with the course of normal biological functions.

Such tissues are, for example: benign and malignant tumors of a solid and cystic nature, papillomas, adenomas and cystadenomas; adenocarcinomas, including those of the cirrhosis type; basal-cell carcinomas; sarcomas, such as, for example, fibrosarcoma, liposarcoma, myxosarcoma, rhabdomyosarcoma, chondrosarcoma, lymphosarcoma and reticulosarcoma, as well as Hodgkin's disease; embryonic tumours, such as, for example, neuroblastoma, nephroblastoma, teratoma, adamantinoma and retroblastoma, haemangioma, chordoma, odontoma and craniopharyngioma; hamartomas, such as, for example, lymphoangioma, exostoses and neurofibromatoses; melanomas; lymphomas; hepatoblastomas; mastocarcinoma; cervical carcinoma; choriocarcinoma and adrenoacanthoma; leiomyoma and andreoblastoma; arrhenoblastoma; Sertoli cell tumour; granulosa and theca cell tumour; germinoma and seminoma and cancer of the vulva; carcinoma of the bladder, prostate carcinoma and adenocarcinoma; tumours caused by schistosomiasis, haemangioblastoma, osteoblastoma and Ewing's tumour; fungoid mucosis; Burkitt's tumour; basaloma, fibroma and, above all, the metastases of all tumour forms which are accessible via surgical intervention using a local injection. Of particular interest among the tissues identified above are those designated as basal-cell carcinomas, fibrosarcoma, haemangioma, odontoma, exostoses and neurofibromatoses and melanomas.

The usefulness of the subject matter of the invention for the treatment of tumours can be demonostarated using test animals as rats, mice, rabbits or dogs in which tumors, such as lymphom EL4, lymphon P 815, acites L 1210. Sacroma Lewis-Lung and Sacroma 180 have been transplanted.

The subject matter of the invention can also be found to be effective in rats, mice, rabbits and dogs for the treatment of tumours at a dosage of 20 to 100 mg/kg locally, preferably subsutaneous, intracutaneous, intratumoral and peritumoral application.

The compounds according to the invention also exhibit therapeutically valuable actions in the case of osteosarcoma; however, in this case the compounds must be injected under a pressure of up to 600 atmospheres gauge using a special device.

In addition, the compounds according to the invention can be used for fibrotic tissues of every type, in particular for the treatment of keloids, Ulcera crura, burn ulcers, decubital ulcers as well as clavi and onychomycoses and scar tissue and for the therapy and prophylaxis of emboli and thromboses.

The compounds according to the invention can also be used for resolving moles, atheromas and lipomas and for removing deep abscesses which, under certain circumstances, are fistulous.

The compounds according to the invention can additionally be used for the regeneration of caveromas and tuberculomas.

The compounds according to the invention can also be used for the scar-free regeneration of tissue defects in the case of leprosy and other skin, mucous membrane and epithelium defects of various origins, above all those which are caused by infections by bacteria, fungi and pathogens of tropical diseases, such as, for example, those of leichmaniasis, framboesia, pinta and the like.

The present invention provides a pharmaceutical composition containing an active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or isotonic aqueous solution.

The invention also provides a medicament in dosage unit form comprising a compound of the invention.

"Medicament" as used in this specification means physically discrete coherent portions suitable for medical administration. "Medicament in dosage unit form" as used in this specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The pharmaceutical compositions which are ointments, pastes, creams and gels can, for example, contain the usual diluents e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils for example ground nut oil, glycerol, tetraydrofururyl alcohol, polyethylene glycols and fatty acid esters of sorbitol or mixtures thereof.

For parenteral administration, solutions and emulsions should be sterile, and, if appropriate, blood-isotonic.

Preferred injection solutions are those having a pH of from 7 to 9.5 most preferably from 8 to 9. The compounds of the invention which are free acids may be conveniently dissolved in dilute physiologically acceptable bases and then brought to the required pH by the addition of a dilute physiologically acceptable acid.

Examples of physiologically acceptable bases which may be mentioned are inorganic hydroxides, carbonates and bicarbonates, in particular those of sodium and potassium. Examples of physiologically acceptable acids which may be mentioned are organic acids, such as citric acid, oxalic acid, lactic acid, benzoic acid, salicyclic acid and acetic acid, or also inorganic acids, such as, for example, dilute hydrochloric or sulphuric acid.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives.

The pharmaceutical compositions according to the invention generally contain from 1 to 90, usually from 5 to 50% of the active ingredient by weight of the total composition.

In addition to a compound of the invention, the pharmaceutical compositions and medicaments according to the invention can also contain other pharmaceutically active compounds. They may also contain a plurality of compound of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted, by virtue of their shape or packaging, for medical administration and may be, for example, any of the following: ampoules. Some of these forms may be made up for delayed release of the active ingredient. Some, such as ampoules include a protective envelope which renders the portions of the medicament physically discrete and coherent.

The preferred daily dose for administration of the medicaments of the invention is from 50 mg to 5 g of active ingredient most preferably from 100 mg to 2 g of active ingredient.

The production of the above mentioned pharmaceutical compositions and medicaments is carried out by any method known in the art, for example, by mixing the active ingredient(s) with the diluent(s) to form a pharmaceutical composition (e.g. a solution or suspension) and then forming the composition into the medicament (e.g. ampoules of injection solution or suspension).

This invention further provides a method of combating the above mentioned diseases in warm-blooded animals, which comprises administering to the animals a compound of the invention alone or in admixture with a diluent or in the form of a medicament according to the invention.

It is envisaged that these active compounds will be administered parenterally (for example intramuscularly, intracutaneously, subcutaneously, intratumorally or peritumorally), topically, preferably intracutaneously, subcataneously, intratumorally and pertumorally. Preferred pharmaceutical compositions and medicaments are therefore those adapted for local administration, such as injection solutions and suspensions, ointments, gels, lotions and creams. Administration in the method of the invention is preferably subscutaneous, intracutaneous, intratumoral and peritumoral.

In general it has proved advantageous to administer amounts of from 1 mg to 100 mg, preferably from 2 to 40 mg per kg of body weight per day to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some cases suffice to use less than the above mentioned minimum dosage rate, whilst other cases the upper limit mentioned must be exceeded to achieve the desired results. Where larger amounts are administered it can be advisable to divide these into several individual administrations over the course of the day.

The examples which follow were carried out in accordance with the following general procedures:

0.025 mol of the aminoacid to be subjected to condensation is suspended in 10 ml of acetone, 25 ml of 1 N NaOH are added, whilst stirring, and the solution formed is mixed with a suspension of the appropriately substituted 5(4H)-oxazolone in acetone. The mixture is stirred at room temperature for ½ to 20 hours, depending on the reactivity of the aminoacid. 25 ml of 1 N HCL are then added to the filtered reaction solution and the acetone is distilled off in vacuo. The desired end product crystallises out of the aqueous phase and is recrystallised from aqueous alcohol.

In the examples given below, the optical rotation was measured at c=2 in dimethylformamide.

The melting points were determined in a Tottoli apparatus and are uncorrected.

EXAMPLE 1

N-Acetyldehydrophenylalanyl-D-proline is obtained from 2-methyl-4-benzylidene-5(4H)-oxazolone and D-proline. Melting point 151°-153° C.; $[\alpha]_D^{20} -69.6°$; yield 55% of theory.

$C_{16}H_{18}N_2O_4$ calculated: C 61.72%, H 6.15%, N 9.0%; found: C 61.75%, H 6.30%, N 8.94%.

EXAMPLE 2

N-Acetyldehydrophenylalanyl-D-tyrosine is obtained from 2-methyl-4-benzylidene-5(4H)-oxazolone and D-tyrosine. Melting point 210° C.; $[\alpha]_D^{20} -43.4°$ (c=2; pyridine); yield 61.3% of theory.

$C_{20}H_{20}N_2O_5$ calculated: C 65.21%, H 5.47%, N 7.60%, found: C 64.56%, H 5.86%, N 7.77%.

EXAMPLE 3

N-Acetyldehydrophenylalanyl-L-methionine is obtained from 2-methyl-4-benzylidene-5(4H)-oxazolone and L-methionine. Melting point 91°-93° C., $[\alpha]_D^{20} -74.4°$; yield 70% of theory.

$C_{16}H_{20}N_2O_4S$ calculated: C 57.12%, H 5.99%, N 8.33%, S 9.53%; found: C 57.02%, H 6.03%, N 8.40%, S 9.46%.

EXAMPLE 4

N-Acetyldehydrophenylalanyl-L-aspartic acid is obtained from 2-methyl-4-benzylidene-5(4H)-oxazolone and L-aspartic acid. Melting point 182°-184° C.; $[\alpha]_D^{20} -46.65°$; yield 63.5% of theory.

$C_{15}H_{16}N_2O_6 \cdot H_2O$ calculated: C 53.25%, H 5.36%, N 8.28%; found: C 53.48%, H 4.92%, N 8.32%.

EXAMPLE 5

N-Acetyldehydrophenylalanyl-L-glutamine is obtained from 2-methyl-4-benzylidene-5(4H)-oxazolone and L-glutamine. Melting point 188° C.; $[\alpha]_D^{20} -74.5°$; yield 54% of theory.

$C_{16}H_{19}N_3O_5$ calculated: C 57.65%, H 5.75%, N 12.61%; found: C 58.17%, H 5.79%, N 13.16%.

EXAMPLE 6

N-Acetyldehydrophenylalanyl-DL-3-fluoroalanine is obtained from 2-methyl-4-benzylidene-5(4H)-oxazolone and D,L-3-fluoroalanine. Melting point 180° C. (decomposition); yield 58.7% of theory.

$C_{14}H_{15}FN_2O_4$ calculated: C 57.14%, H 5.14%, F 6.46%, N 9.52%; found: C 57.22%, H 5.22%, F 6.30%, N 9.58%.

EXAMPLE 7

N-Acetyldehydrophenylalanyl-L-serine is obtained from 2-methyl-4-benzylidene-5(4H)-oxazolone and L-serine. Melting point 179° C. (decomposition); $[\alpha]_D^{20} +1.15°$; yield 48.5% of theory.

$C_{14}H_{16}N_2O_5$ calculated: C 57.53%, H 5.52%, N 9.58%; found: C 57.48%, H 5.47%, N 9.66%.

EXAMPLE 8

N-Acetyldehydrophenylalanyl-L-(p-nitrophenyl)alanine is obtained from 2-methyl-4-benzylidene-5(4H)-oxazolone and L-4-nitrophenylalanine. Melting point 192°–193° C. (from ethanol/petroleum ether/isopropyl ether); $[\alpha]_D^{20}-110.7°$; yield 70.3% of theory.

$C_{20}H_{19}N_3O_6$ calculated: C 60.45%, H 4.82%, N 10.58%; found: C 60.40%, H 4.90%, N 10.43%.

EXAMPLE 9

N-Acetyldehydrophenylalanyl-DL-(p-chlorophenyl)alanine is obtained from 2-methyl-4-benzylidene-5(4H)-oxazolone and DL-(4-chlorophenyl)alanine. Melting point 214°–215° C. (from ether/petroleum ether); yield 66.9% of theory.

$C_{20}H_{19}ClN_2O_4$ calculated: C 62.10%, H 4.95%, Cl 9.17%, N 7.24%; found: C 62.39%, H 5.02%, Cl 9.14%, N 7.11%.

EXAMPLE 10

N-Trifluoroacetyldehydrophenylalanyl-L-tyrosine is obtained from 2-trifluoromethyl-4-benzylidene-5(4H)-oxazolone and L-tyrosine. Melting point 165°–175° C.; $[\alpha]_D^{20}-57.4°$ (c=1; dimethylformamide); yield 91% of theory.

$C_{20}H_{17}F_3N_2O_5$ calculated: C 56.87%, H 4.06%, F 13.50%, N 6.63%; found: C 56.92%, H 4.05%, F 13.40%, N 6.61%.

EXAMPLE 11

N-Acetyldehydro(p-methylphenyl)alanyl-L-tyrosine is obtained from 2-methyl-4-(4-methylbenzylidene)-5(4H)-oxazolone and L-tyrosine. Melting point 220°–221° C.; $[\alpha]_D^{20}-38.5°$; yield 47.6% of theory.

$C_{21}H_{22}N_2O_5$ calculated: C 65.95%, H 5.80%, N 7.33%; found: C 65.96%, H 5.80%, N 7.16%.

EXAMPLE 12

N-Benzoyl-2-cyclohexylideneglycyl-L-tyrosine is obtained from 2-phenyl-4-cyclohexylidene-5(4H)-oxazolone and L-tyrosine. Melting point 121° C.; $[\alpha]_D^{20}-0.5°$; yield 75.8% of theory.

$C_{24}H_{26}N_2O_5$ calculated: C 68.23%, H 6.20%, N 6.63%; found: C 68.16%, H 6.18%, N 6.65%.

EXAMPLE 13

N-Benzoyl-2-(2-cyclohexenylidene)glycyl-L-tyrosine is obtained from 2-phenyl-4-(2-cyclohexenylidene)-5(4H)-oxazolone and L-tyrosine. Melting point 126° C.; $[\alpha]_D^{20}-5.7°$; yield 60% of theory.

$C_{24}H_{24}N_2O_5$ calculated: C 68.56%, H 5.75%, N 6.66%; found: C 68.46%, H 5.70%, N 6.56%.

EXAMPLE 14

N-Acetyldehydro-3-(2-furyl)alanyl-D-tyrosine is obtained from 2-methyl-4-(2-furfurylidene)-5(4H)-oxazolone Melting point 217° C. (ethanol/petroleum ether); $[\alpha]_D^{20}-29.1°$; yield 31% of theory.

$C_{18}H_{18}N_2O_6$ calculated: C 60.33%, H 5.06%, N 7.82%; found: C 60.37%, H 5.11%, N 7.70%.

EXAMPLE 15

N-Acetyldehydro-3-cinnamenylalanyl-L-tyrosine is obtained from 2-methyl-4-(3-phenyl-2-propenylidene)-5(4H)-oxazolone and L-tyrosine. Melting point 220°–221° C.; $[\alpha]_D^{20}-44.2°$; yield 57.3% of theory.

$C_{22}H_{22}N_2O_5$ calculated: C 66.99%, H 5.62%, N 7.10%, found: C 66.80%, H 5.64%, N 7.06%.

EXAMPLE 16

N-Acetyldehydro-3-(2-naphthyl)alanyl-L-tyrosine is obtained from 2-methyl-4-(2-naphthylmethylene)-5(4H)-oxazolone and L-tyrosine. Melting point 221°–222° C. (precipitate from ethyl acetate/isopropanol with petroleum ether); $[\alpha]_D^{20}-11.6°$ (c=2; from methanol); yield 55.7% of theory.

$C_{24}H_{22}N_2O_5$ calculated: C 68.89%, H 5.30%, N 6.70%; found: C 69.04%, H 5.37%, N 6.65%.

EXAMPLE 17

N-Benzoyldehydro-3-cyclohexylalanyl-L-tyrosine is obtained from 2-phenyl-4-cyclohexylmethylene-5(4H)-oxazolone and L-tyrosine. Melting point 126°–128° C.; $[\alpha]_D^{20}+0.8°$ (c=1; dimethylformamide); yield 60.3% of theory.

$C_{25}H_{28}N_2O_5$ calculated: C 68.79%, H 6.46%, N 6.42%; found: C 68.59%, H 6.32%, N 6.24%.

EXAMPLE 18

N-Acetyldehydrophenylalanyl-3-(5-methyl-2-thienyl)dehydroalanine is obtained from 4-(5-methylthenylidene)-2-(1-acetamido-2-phenylvinyl)-5(4H)oxazolone. Melting point: 193°–194° C.; yield: 40% of theory.

$C_{19}H_{18}N_2O_4S$ calculated: C 61.61%, H 4.90%, N 7.56%, S 8.66%; found: C 61.54%, H 4.96%, N 7.55%, S 8.70%.

EXAMPLE 19

N-Acetyldehydro-3-(2-thienyl)alanyldehydro-3-(2-thienyl)alanine is obtained from 2-[1-acetamido-2-(2-thienyl)vinyl]-4-(2-thenylidene)-5(4H)oxazolone. Melting point: 218° C.; yield 80% of theory.

$C_{16}H_{14}N_2O_4S_2$ calculated: C 53.02%, H 3.89%, N 7.73%, S 17.69%; found: C 52.99%, H 3.94%, N 7.96%, S 17.70%.

EXAMPLE 20

N-Acetyldehydro-3-(2-thienyl)alanyldehydro-3-(4-nitrophenyl)alanine is obtained from 4-(4-nitrobenzylidene)-2-[1-acetamido-2-(2-thienyl)vinyl]-5(4H)oxazolone. Melting point: 196°–197° C.; yield: 55.7% of theory.

$C_{18}H_{15}N_3O_6S$ calculated: C 53.86%, H 3.77%, N 10.47%, S 7.99%; found: C 53.80%, H 3.81%, N 10.52%, S 7.85%.

EXAMPLE 21

N-(3,4,5-Trimethoxycinnamoyl)dehydro-3-(2-thienyl)alanyl-L-tyrosine is obtained from 2-[2-(3,4,5-trimethoxyphenyl)vinyl]-4-(2-thenylidene)-5(4H)oxazolone and L-tyrosine. Melting point: 148°–150° C.; yield: 92.2% of theory.

$C_{28}H_{28}N_2O_8S$ calculated: C 60.86%, H 5.11%, N 5.07%, S 5.80%; found: C 60.74%, H 5.15%, N 5.07%, S 5.79%.

EXAMPLE 22

N-Crotonoyldehydro-3-(2-thienyl)alanyl-L-tyrosine is obtained from 2-(1-propenyl)-4-(2-thenylidene)-5(4H)-oxazolone and L-tyrosine. Melting point: 157° C.; yield: 51% of theory.

$C_{20}H_{20}NO_5S$ calculated: C 59.99%, H 5.03%, N 7.00%, S 8.01%; found: C 60.34%, H 4.97%, N 6.63%, S 7.51%.

EXAMPLE 23

N-Acetyldehydro-3-(5-nitro-2-thienyl)alanyl-L-tyrosine is obtained from 2-methyl-4-(5-nitro-2-thenylidene)-5(4H)-oxazolone and L-tyrosine. Melting point: 148°–157° C.; yield: 54.6% of theory.

$C_{18}H_{17}N_3O_7S$ calculated: C 51.55%, H 4.09%, N 10.02%, S 7.65%; found: C 51.36%, H 4.11%, N 10.01%, S 7.64%.

EXAMPLE 24

N-(2-Thenoyl)dehydro-3-(2-thienyl)alanyl-L-tyrosine is obtained from 2-(2-thienyl)-4-(2-thenylidene)-5(4H)-oxazolone and L-tyrosine. Melting point: 140°–150° C.; yield: 72% of theory.

$C_{21}H_{18}N_2O_5S_2$ calculated: C 57.00%, H 4.10%, N 6.33%, S 14.49%; found: C 57.01%, H 4.28%, N 6.35%, S 14.12%.

EXAMPLE 25

N-Acetyldehydro-3-(2-thienyl)alanyl-O-methyl-L-tyrosine is obtained from 2-methyl-4-(2-thenylidene)-5(4H)oxazolone and O-methyl-L-tyrosine. Melting point: 236° C.; yield: 90% of theory.

$C_{19}H_{20}N_2O_5S$ calculated: C 53.75%, H 5.19%, N 7.21%, S 8.25%; found: C 53.83%, H 5.36%, N 7.23%, S 8.30%.

EXAMPLE 26

N-Acetyldehydro-3-(2-thienyl)alanyl-L-glutamic acid is obtained from 2-methyl-4-(2-thenylidene)-5(4H)oxazolone and L-glutamic acid. Melting point: 205° C. (decomposition); yield: 76.5% of theory.

$C_{14}H_{16}N_2O_6S$ calculated: C 49.40%, H 4.74%, N 8.23%, S 9.42%; found: C 49.61%, H 4.76%, N 8.16%, S 9.59%.

EXAMPLE 27

N-Trifluoroacetyldehydrophenylalanyl-L-tyrosine tert.-butyl ester is obtained from 2-trifluoromethyl-4-benzylidene-5(4H)-oxazolone and L-tyrosine tert.-butyl ester. The reaction is carried out in dimethylformamide without NaOH. Melting point 182°–183° C.; $[\alpha]_D^{20} - 29.7°$ (c=1; dimethylformamide); yield 84% of theory.

$C_{24}H_{25}F_3N_2O_5$ calculated: C 60.24%, H 5.27%, F 11.91%, N 5.86%; found: C 60.30%, H 5.30%, F 11.90%, N 5.93%.

EXAMPLE 28

N-Benzoyldehydro-3-(2-thienyl)alanyl-L-proline is obtained from 2-phenyl-4-(2-thenylidene)-5(4H)-oxazolone and L-proline. Melting point 125° C. (ill-defined): $[\alpha]_D^{20} + 2.0°$; yield 52% of theory.

$C_{19}H_{18}N_2O_4S$ calculated: C 61.60%, H 4.90%, N 7.56%, S 8.66%; found: C 61.59%, H 4.80%, N 7.50%, S 8.79%.

EXAMPLE 29

N-Acetyldehydrophenylalanin-(1-carboxy-1-cyclopentyl)amide is obtained from 2-methyl-4-benzylidene-5(4H)-oxazolone and 1-aminocyclopentanecarboxylic acid. Melting point: 217° C. (decomposition); yield 50.7% of theory.

$C_{17}H_{20}N_2O_4$ calculated: C 64.54%, H 6.37%, N 8.86%; found: C 64.85%, H 6.55%, N 8.41%.

EXAMPLE 30

N-Acetyldehydro-3-(2-thienyl)alanyl-L-tyrosine is obtained from 2-methyl-4-(2-thenylidene)-5(4H)-oxazolone and L-tyrosine. Melting point 227°–228° C.; $[\alpha]_D^{20} - 36.75°$; yield 71.06% of theory.

$C_{18}H_{18}N_2O_5S$ calculated: C 57.74%, H 4.85%, N 7.48%, S 8.56%; found: C 57.61%, H 4.84%, N 7.49%, S 8.625.

EXAMPLE 31

N-Phenacetyldehydro-3-(2-thienyl)alanyl-L-tyrosine tert.-butyl ester is obtained from 2-benzyl-4-(2-thenylidene)-5(4H)-oxazolone and L-tyrosine tert.-butyl ester. Melting point 110°–120° C. (crude product); yield 51.5% of theory. This compound was further processed by stirring for ½ hour with trifluoroacetic acid to give N-phenacetyldehydro-3-(2-thienyl)alanyl-L-tyrosine Melting point 135°–140° C. (decomposition); $[\alpha]_D^{20} - 41°$; yield 49% of theory.

$C_{24}H_{22}N_2O_5S$ calculated: C 63.98%, H 4.92%, N 6.22%, S 7.12%; found: C 63.79%, H 4.82%, N 6.29%, S 7.07%.

EXAMPLE 32

N-Benzoyldehydro-3-(2-thienyl)alanyl-L-tyrosine is obtained from 2-phenyl-4-(2-thenylidene)-5(4H)-oxazolone and L-tyrosine. Melting point 135° C. (ill-defined); yield 41.2% of theory.

$C_{23}H_{20}N_2O_5S$ calculated: C 63.29%, H 4.62%, N 6.43%, S 7.34%; found: C 63.25%, H 4.67%, N 6.37%, 7.38%.

EXAMPLE 33

N-Benzoyldehydro-3-(2-thienyl)alanyl-L-(p-nitrophenyl)-alanine is obtained from 2-phenyl-4-(2-thenylidene)-5(4H)-oxazolone and 4-nitro-L-phenylalanine. Melting point 125° C. (ill-defined); $[\alpha]_D^{20} - 67.3°$; yield 60% of theory.

$C_{23}H_{19}N_3O_6S$ calculated: C 59.35%, H 4.11%, N 9.03%, S 6.89%; found: C 59.39%, H 4.36%, N 9.01%, S 6.71%.

EXAMPLE 34

N-Nicotinoyldehydro-3-(2-thienyl)alanyl-L-tyrosine is obtained from 2-(3-pyridyl)-4-(2-thenylidene)-5(4H)-oxazolone and L-tyrosine. Melting point 160° C. (ill-defined); $[\alpha]_D^{20} - 8.35°$; yield 50% of theory.

$C_{22}H_{19}N_3O_5S$ calculated: C 60.40%, H 4.38%, N 9.60%, S 7.33%; found: C 60.57%, H 4.58%, N 9.75%, S 7.32%.

EXAMPLE 35

N-(3-Trifluoromethylbenzoyl)dehydro-3-(2-thienyl)alanyl-L-tyrosine is obtained from 2-(3-trifluoromethylphenyl)-4-(2-thenylidene)-5(4H)-oxazolone and L-tyrosine. Melting point 125° C. (ill-defined); $[\alpha]_D^{20} - 8.9°$; yield 48% of theory.

$C_{24}H_{19}F_3N_2O_5S$ calculated: C 57.14%, H 3.80%, F 11.30%, N 5.55%, S 6.36%; found: C 56.95%, H 3.81%, F 11.40%, N 5.45%, S 6.45%.

EXAMPLE 36

N-Nicotinoyldehydro-3-(2-thienyl)alanyl-L-(p-nitrophenyl)alanine is obtained from 2-(3-pyridyl)-4-(2- thenylidene)-5(4H)-oxazolone and L-4-nitrophenylalanine. Melting point 197° C. (decomposition); $[\alpha]_D^{20} -98°$; yield 75% of theory.

$C_{22}H_{18}N_4O_6S$ calculated: C 56.64%, H 3.89%, N 12.01%, S 6.87%; found: C 56.55%, H 3.91%, N 12.05%, S 6.89%.

EXAMPLE 37

N-Benzoyl-3-methyl-3-(2-thienyl)dehydroalanyl-L-tyrosine is obtained from 2-phenyl-4-(α-methyl-2-thenylidene)-5(4H)-oxazolone and L-tyrosine. Melting point 128° C.; $[\alpha]_D^{20} +15.6°$; yield 66.7% of theory.

$C_{24}H_{22}N_2O_5S$ calculated: C 63.98%, H 4.92%, N 6.22%, S 7.12%; found: C 64.14%, H 4.93%, N 6.34%, S 7.03%.

EXAMPLE 38

N-Acetyldehydro-3-(2-thienyl)alanyl-D-tyrosine is obtained from 2-methyl-4-(2-thenylidene)-5(4H)-oxazolone and D-tyrosine. Melting point 221°-222° C.; $[\alpha]_D^{20} +36.8°$; yield 51.49% of theory.

$C_{18}H_{18}N_2O_5S$ calculated: C 57.74%, H 4.85%, N 7.48%, S 8.56%; found: C 57.83%, H 4.89%, N 7.44%, S 8.67%.

EXAMPLE 39

N-Benzoyldehydroisoleucyl-L-tyrosine is obtained from 2-phenyl-4-(1-methylpropylidene)-5(4H)-oxazolone and L-tyrosine. Melting point 107° C.; $[\alpha]_D^{20} -12.1°$; yield 31.5% of theory.

$C_{22}H_{24}N_2O_5$ calculated: C 66.65%, H 6.10%, N 7.07%; found: C 66.57%, H 6.17%, N 6.90%.

EXAMPLE 40

N-Benzoyl-3-methyl-3-cinnamenyldehydroalanyl-L-tyrosine is obtained from 2-phenyl-4-(1-methyl-3-phenyl-2-propenylidene)-5(4H)-oxazolone and L-tyrosine. Melting point 130° C.; $[\alpha]_D^{20} -5.5°$; yield 96% of theory.

$C_{28}H_{26}N_2O_5$ calculated: C 71.47%, H 5.57%, N 5.95%; found: C 71.60%, H 5.57%, N 5.87%.

EXAMPLE 41

N-Cinnamoyldehydrophenylalanyl-L-tyrosine is obtained from 2-cinnamenyl-4-benzylidene-5(4H)-oxazolone and L-tyrosine. Melting point 172°-174° C.; $[\alpha]_D^{20} -24°$; yield 30% of theory.

$C_{27}H_{24}N_2O_5$ calculated: C 71.94%, H 5.3%, N 6.14%; found: C 70.85%, H 5.39%, N 6.16%.

EXAMPLE 42

N-Acetyldehydrophenylalanyldehydro-(3-chlorophenyl)-alanyl-L-tyrosine is obtained from 2-(1-acetamido-2-phenylethylene)-4-(3-chlorobenzylidene)-5(4H)-oxazolone and L-tyrosine. Melting point 191°-193° C.; $[\alpha]_D^{20} -154.3°$ (c=1; dimethylformamide); yield 78.5% of theory.

$C_{29}H_{26}ClN_3O_6$ calculated: C 63.56%, H 4.78%, Cl 6.47%, N 7.67%; found: C 63.69%, H 4.76%, Cl 6.54%, N 7.70%.

EXAMPLE 43

N-Acetyldehydrophenylalanyldehydro-(4-nitrophenyl)alanine 4.5 g (0.0119 mol) of 2-(1-acetamido-2-phenylvinyl)-4-(4-nitrobenzylidene)-5(4H)-oxazolone are suspended in 60 ml of acetone, 31.9 ml of N NaOH are added and the mixture is stirred at room temperature for 100 minutes. After acidifying the reaction solution with 33.5 ml of N HCl, the reaction product precipitates in the analytically pure form. Melting point 181° C.; yield 56.4% of theory.

$C_{20}H_{17}N_3O_6$ calculated: C 60.76%, H 4.33%, N 10.63%; found: C 60.86%, H 4.51%, N 10.46%.

EXAMPLE 44

N-Acetyldehydrophenylalanyldehydro(4-chlorophenyl)alanine is obtained from 2-(1-acetamido-2-phenylvinyl)-4-(4-chlorobenzylidene)-5(4H)-oxazolone. Melting point 177° C.; yield 60.9% of theory.

$C_{20}H_{17}ClN_2O_4$ calculated: C 62.42%, H 4.45%, N 7.28%, Cl 9.21%; found: C 62.49%, H 4.47%, N 7.36%, Cl 9.24%.

EXAMPLE 45

N-Acetyldehydrophenylalanyldehydro(p-fluorophenyl)alanine is obtained from 2-(1-acetamido-2-phenylvinyl)-4-(4-fluorobenzylidene)-5(4H)-oxazolone Melting point 172° C.; yield 65.27% of theory.

$C_{20}H_{17}FN_2O_4 \cdot H_2O$ calculated: C 62.17%, H 4.96%, F 4.92%, N 7.25%; found: C 62.30%, H 4.94%, F 4.70%, N 7.25%.

EXAMPLE 46

N-Acetyldehydrophenylalanyldehydro)4-dimethylaminophenyl)alanine is obtained from 2-(1-acetamido-2-phenylvinyl)-4-(4-dimethylaminobenzylidene)-5(4H)-oxazolone. Melting point 153°-155° C.; yield 36.2% of theory.

$C_{22}H_{23}N_3O_4$ calculated: C 67.16%, H 5.89%, N 10.68%; found: C 67.03%, H 6.00%, N 10.52%.

EXAMPLE 47

N-Acetyldehydrophenylalanyldehydro(3-chlorophenyl)alanine is obtained from 2-(1-acetamido-2-phenylvinyl)-4-(3-chlorobenzylidene)5(4H)-oxazolone. Melting point 183° C.; yield 88.4% of theory.

$C_{20}H_{17}ClN_2O_4$ calculated: C 62.42%, H 4.45%, Cl 9.21%, N 7.28%; found: C 62.54%, H 4.45%, Cl 9.23%, N 7.18%.

In the examples which follow, the reaction was carried out in tetrahydrofurane without NaOH.

EXAMPLE 48

N-Benzoyldehydro-3-(2-thienyl)alanyl-L-tyrosine methyl ester is obtained from 2-phenyl-4-(2-thenylidene)-5(4H)-oxazolone and L-tyrosine methyl ester. Melting point 120° C. (ill-defined); $[\alpha]_D^{20} -4.6°$; yield 95% of theory.

$C_{24}H_{22}N_2O_5S$ calculated: C 63.98%, H 4.92%, N 6.22%, S 7.12%; found: C 63.78%, H 4.93%, N 6.07%, S 7.02%.

EXAMPLE 49

N-Acetyldehydro-3-(2-thienyl)alanyl-L-tyrosine methyl ester is obtained from 2-methyl-4-(2-thenylidene)-5(4H)-oxazolone and L-tyrosine methyl ester. Melting point 243°-245° C.; $[\alpha]_D^{20} -78.1°$ (c=1; dimethylsulphoxide).

$C_{19}H_{20}N_2O_5S$ yield 65% of theory. calculated: C 58.75%, H 5.19%, N 7.21%, S 8.26%; found: C 58.45%, H 5.35%, N 7.17%, S 8.47%.

EXAMPLE 50

N-Acetyldehydro-3-(2-thienyl)alanyl-3-(2-thienyl)-dehydroalanyl-L-tyrosine tert.-butyl ester is obtained from 2-[1-acetamido-2-(2-thienyl)vinyl]-4-(2- thenylidene)-5(4H)-oxazolone and L-tyrosine tert.-butyl ester, analogously to Example 81. Melting point: 158° C.; yield: 94% of theory.

$C_{29}H_{31}N_3O_6S_2$ calculated: C 59.88%, H 5.37%, N 7.22%, S 11.03%; found: C 60.01%, H 5.415, N 7.15%, S 11.08%.

EXAMPLE 51

N-Acetyldehydro-3-(2-thienyl)alanyl-3-(2-thienyl)-dehydroalanyl-L-tyrosine benzyl ester is obtained from 2-[1-acetamido-2-(2-thienyl)vinyl]-4-(2-thenylidene)-5-(4H)oxazolone and L-tyrosine benzyl ester, analogously to Example 81. Melting point: 130° C.; yield: 83% of theory.

$C_{32}H_{29}N_3O_6S_2$ calculated: C 62.42%, H 4.75%, N 6.82%, S 10.42%; found: C 62.52%, H 4.68%, N 6.83%, S 10.40%.

EXAMPLE 52

N-Acetyldehydro-3-(2-thienyl)alanyl-3-(2-thienyl)-dehydroalanyl-L-tyrosine methyl ester is obtained from 2-[1-acetamido-2-(2-thienyl)vinyl]-4-(2-thenylidene)-5(4H)oxazolone and L-tyrosine methyl ester, analogously to Example 81. Melting point: 155° C.; yield: 96% of theory.

$C_{26}H_{25}N_3O_6S_2$ calculated: C 57.86%, H 4.67%, N 7.79%, S 11.89%; found: C 58.08%, H 4.79%, N 7.75%, S 11.88%.

EXAMPLE 53

N-Acetyldehydro-3-(2-thienyl)alanyl-N-methyl-L-tyrosine methyl ester is obtained from 2-methyl-4-(2-thenylidene)-5(4H)oxazolone and N-methyl-L-tyrosine methyl ester. Melting point: 102° C.; yield: 38.9% of theory.

$C_{20}H_{22}N_2O_5S.H_2O$ calculated: C 58.38%, H 5.63%, N 6.81%, S 7.79%; found: C 58.28%, H 5.59%, N 6.89%, S 8.15%.

EXAMPLE 54

N-Acetyldehydro-3-(3-thienyl)alanyl-N-methyl-L-tyrosine is obtained from the above compound by boiling with NaOH. Melting point: 150°–170° C.; yield: 72.6% of theory.

$C_{19}H_{20}N_2O_5S$ calculated: C 58.75%, H 5.19%, N 7.21%, S 8.25%; found: C 58.62%, H 5.36%, N 7.08%, S 8.35%.

EXAMPLE 55

N-Acetyldehydro-3-(3-nitro-4-hydrophenyl)alanyl-L-tyrosine tert.-butyl ester is obtained from 2-methyl-4-(3-nitro-4-acetoxybenzylidene)-5 (4H)oxazolone and L-tyrosine tert.-butyl ester. Melting point: 148°–151° C.; yield: 45.5% of theory.

$C_{24}H_{27}N_3O_8$ calculated: C 59.37%, H 5.61%, N 8.66%; found: C 59.43%, H 5.71%, N 8.54%.

EXAMPLE 56

N-Acetyldehydro-3-(3-nitro-4-hydroxyphenyl)alanyl-L-tyrosine is obtained from the above compound by stirring with trifluoroacetic acid. Melting point: 145° C.; yield: 93% of theory.

$C_{21}H_{22}N_3O_8$ calculated: C 56.76%, H 4.99%, N 9.24%; found: C 56.88%, H 5.09%, N 9.31%.

EXAMPLE 57

N-Benzoyldehydro-3-(4-pyridyl)alanyl-L-tyrosine methyl ester is obtained from 2-phenyl-4-(4-pyridinyl-methylene)-5(4H)-oxazolone and L-tyrosine methyl ester. Melting point: 155°–160° C.; yield: 33.7% of theory.

$C_{25}H_{23}N_3O_5.H_2O$ calculated: C 66.07%, H 5.32%, N 9.25%; found: C 66.17%, H 5.59%, N 9.25%.

EXAMPLE 58

N-Benzoyldehydro-3-(4-pyridyl)alanyl-L-tyrosine is obtained from the above compound by boiling with dilute sodium hydroxide solution. Melting point: 162°–166° C.; yield: 54.3% of theory.

$C_{24}H_{21}N_3O_5$ calculated: C 66.81%, H 4.91%, N 9.74%; found: C 66.63%, H 5.13%, N 9.77%.

EXAMPLE 59

N-(4-Nitrophenyl)acetyldehydro-3-(2-thienyl)alanyl-L-tyrosine methyl ester Melting point: 218°–222° C.; yield: 55.7% of theory.

$C_{25}H_{23}N_3O_7S$ calculated: C 58.93%, H 4.55%, N 8.25%, S 6.29%; found: C 58.82%, H 4.55%, N 8.13%, S 6.11%.

EXAMPLE 60

N-(4-Nitrophenyl)acetyldehydro-3-(2-thienyl)alanyl-L-tyrosine is obtained from the above compound by boiling with dilute sodium hydroxide solution. Melting point: 161°–166° C.; yield: 41.6% of theory.

$C_{24}H_{21}N_3O_7S$ calculated: C 58.17%, H 4.27%, N 8.48%, S 6.47%; found: C 58.26%, H 4.44%, N 8.45%, S 6.63%.

EXAMPLE 61

N-Acetyldehydro-3-(2-thienyl)alanyl-3-(2-thienyl)-dehydroalanyl-L-tyrosine tert.-butyl ester is obtained from 2-[1-acetamido-2-(2-thienyl)vinyl]-4-(2-thenylidene)-5-(4H) oxazolone and L-tyrosine tert.-butyl ester. Melting point: 158° C. (decomposition); yield: 94% of theory.

$C_{29}H_{31}N_3O_6S_2$ calculated: C 59.88%, H 5.37%, N 7.22%, S 11.03%; found: C 60.01%, H 5.41%, N 7.15%, S 11.08%.

EXAMPLE 62

N-Acetyldehydro-3-(2-thienyl)alanyl-3-(2thienyl)-dehydroalanyl-L-tyrosine is obtained from the above compound by adding glacial acetic acid/HCl. Melting point: 189° C. (decomposition); yield: 88% of theory.

$C_{25}H_{25}N_3O_6S_2$ calculated: C 57.13%, H 4.91%, N 7.99%, S 12.20%; found: C 56.90%, H 4.63%, N 7.92%, S 12.04%.

EXAMPLE 63

N-Benzoyldehydroisoleucyl-L-tyrosine methyl ester is obtained from 2-phenyl-4-(1-methylpropylidene-5(4H9-oxazolone and tryosine methyl ester. Melting point: 163°–165° C.; yield: 35.5% of theory.

$C_{33}H_{26}N_2O_5$ calculated: C 67.30%, H 6.38%, N 6.83%; found: C 67.23%, H 6.35%, N 6.82%.

EXAMPLE 64

N-(2-Thienyl)acetyldehydro-3-(2-thienyl)alanyl-L-tyrosine tert.-butyl ester is obtained from 2-(2-thienylmethyl)-4-(2-thenylidene)-5(4H)-oxazolone and L-tyrosine tert.-butyl ester. Melting point: 105° C.; yield: 85% of theory.

$C_{26}H_{28}N_2O_5S_2$ calculated: C 60.91%; H 5.50%, N 5.47%, S 12.51%; found: C 61.02%, H 5.575, N 5.60%, S 12.36%.

EXAMPLE 65

N-(2-Thienyl)acetyldehydro-3-(2-thienyl)alanyl-L-tyrosine is obtained from the above compound by adding glacial acetic acid/hydrochloric acid. Melting point: 110° C.; yield: 95% of theory.

$C_{22}H_{20}N_2O_5S_2$ calculated: C 57.88%, H 4.41%, N 6.14%, S 14.05%; found: C 57.64%, H 4.52%, N 6.06%, S 13.90%.

EXAMPLE 66

N-(2Thienyl)acetyldehydro-3-(2-thienyl)alanyl-L-tyrosine benzyl ester is obtained from 2-(2-thienylmethyl)-4-(2-thenylidene)-5(4H)-oxazolone and L-tyrosine benzyl ester. Melting point: 95° C.; yield: 83% of theory.

$C_{29}H_{26}N_2O_5S_2$ calculated: C 63.71%, H 4.795, N 5.13%, S 11.74%; found: C 63.85%, H 4.805, N 5.06%, S 11.69%.

EXAMPLE 67

N-(2-Thienyl)acetyldehydro-3-(2-thienyl)alanyl-L-tyrosine methyl ester is obtained from 2-(2-thienylmethyl)-4-(2-thenylidene)-5(4H)-oxazolone and L-tyrosine methyl ester. Melting point: 200° C. (decomposition); yield: 80% of theory.

$C_{23}H_{22}N_2O_5S_2$ calculated: C 58.70%, H 4.71%, N 5.95%, S 13,63%; found: C 58.79%, H 4.76%, N 5.95%, S 13.50%.

EXAMPLE 68

N-Benzoyldehydro-3-(2-thienyl)alanyl-L-tyrosine benzyl ester is formed from the acid and benzyl alcohol by heating to 80° C. for ½ hour in the presence of hydrogen chloride. Melting point 95° C. (ill-defined); $[\alpha]_D^{20}$ −2.0°; yield 79% of theory.

$C_{30}H_{26}N_2O_5S$ calculated: C 68.42%, H 4.98%, N 5.32%, S 6.09%; found: C 68.42%, H 4.96%, N 5.30%, S 6.02%.

The salts below were prepared from the dehydroamino acid by allowing the acid to stand with three times the amount of amine and diluting the mixture with methanol and evaporating it to dryness.

EXAMPLE 69

The slt of N-acetyldehydro-3-(2-thienyl)alanyl-L-tyrosine with piperidine Melting point: 184°–186° C.; yield: 58.80% of theory.

$C_{23}H_{29}N_3O_5S$ calculated: C 60.11%, H 6.36%, N 9.14%, S 6.98%; found: C 60.29%, H 6.27%, N 9.33%, S 7.17%,

EXAMPLE 70

The salt of N-acetyldehydro-3-(2-thienyl)alanyl-L-tyrosine with ethylenediamine Melting point: 148°–158° C.; yield: 98.9% of theory.

$C_{38}H_{44}N_6O_{10}S_2$ calculated: C 56.42%, H 5.48%, N 10.39%, S 7.93%; found: C 56.38%, H 5.64%, N 10.26%, S 7.81%.

EXAMPLE 71

The salt of N-acetyldehydro-3-(2-thienyl)alanyl-L-tyrosine with triethanolamine Melting point: 125°–130° C.; yield: 84.1% of theory.

$C_{24}H_{33}N_3O_8S$ calculated: C 55.05%, H 6.35%, N 8.03%, S 6.12%; found: C 54.77%, H 6.30%, N 7.93%, S 6.00%.

EXAMPLE 72

The salt of N-acetyldehydro-3-(2-thienyl)alanyl-L-tyrosine with DL-canavanine Melting point: 165°–173° C.; yield: 90.9% of theory.

$C_{23}H_{30}N_6O_8S$ calculated: C 50.17%, H 5.49%, N 15.27%, S 5.81%; found: C 50.02%, H 5.62%, N 15.35%, S 5.67%.

EXAMPLE 73

The salt of N-acetyldehydro-3-(2-thienyl)alanyl-L-tyrosine with L-arginine Melting point: 125°–140° C.; yield: 79.3% of theory.

$C_{24}H_{32}N_6O_7S$ calculated: C 52.54%, H 5.88%, N 15.32%, S 5.85%; found: C 52.44%, H 6.00%, N 15.31%, S 5.10%.

EXAMPLE 74

The salt of N-acetyldehydro-3-(2-thienyl)alanyl-L-tyrosine with L-lysine Melting point: 174°–182° C.; yield: 96.1% of theory.

$C_{24}H_{32}N_4O_7S$ calculated: C 55.37%, H 6.20%, N 10.76%, S 6.16%; found: C 55.22%, H 6.41%, N 10.87%, S 6.04%.

The amides below were prepared from N-benzoyldehydro-3-(2-thienyl)alanyl-L-tyrosine methyl ester (calledA in the exampls which follow) by allowing a mixture of the ester with the corresponding amines (1 mol of ester per 8 mols of amine) to stand in methanol or tetrahydrofurane and working up the mixture by evaporating and purifying on silica gel (reaction time 3 to 340 hours).

EXAMPLE 75

N-Benzoyldehydro-3-(2-thienyl)alanyl-L-tyrosine amide is obtained from A and ammonia. Melting point 210° C.; $[\alpha]_D^{20}$−62.0°; yield 86% of theory.

$C_{23}H_{21}N_3O_4S$ calculated: C 63.43%, H 4.86%, N 9.65%, S 7.36%; found: C 63.25%, H 4.96%, N 9.59%, S 7.38%.

EXAMPLE 76

N-Benzoyldehydro-3-(2-thienyl)alanyl-L-tyrosine N'-hexylamide is obtained from A and n-hexylamine. Melting point 115° C. (ill-defined); $[\alpha]_D^{20}$−63.4°; yield 80% of theory.

$C_{29}H_{33}N_3O_4S$ calculated: C 67.03%, H 6.40%, N 8.09%, S 6.17%; found: C 67.22%, H 6.51%, N 8.19%, S 6.08%.

EXAMPLE 77

N-Benzoyldehydro-3-(2-thienyl)alanyl-L-tyrosine N'-methylamide is obtained from A and methylamine (aqueous solution). Melting point 145° C. (ill-defined); $[\alpha]_D^{20}$−61.7°; yield 90.2% of theory.

$C_{24}H_{23}N_3O_4S$ calculated: C 64.12%, H 5.16%, N 9.35%, S 7.13%; found: C 64.04%, H 4.99%, N 9.42%, S 7.07%.

EXAMPLE 78

N-Benzoyldehydro-3-(2-thienyl)alanyl-L-tyrosine N'-cyclohexylamide is obtained from A and cyclohexylamine. Melting point 110° C. (ill-defined); $[\alpha]_D^{20}$ −50.9°; yield 44% of theory.

$C_{29}H_{31}N_3O_4S$ calculated: C 67.29%, H 6.04%, N 8.12%, S 6.19%; found: C 67.38%, H 6.33%, N 8.09%, S 5.88%.

EXAMPLE 79

N-Benzoyldehydro-3-(2-thienyl)alanyl-L-tyrosine N',N'-dimethylamide is obtained from A and dimethylamine (aqueous solution). Melting point 130° C. (ill-defined); $[\alpha]_D^{20}$ −2.2°; yield 13% of theory.

$C_{25}H_{25}N_3O_4S$ calculated: C 64.77%, H 5.44%, N 9.06%, S 6.92%; found: C 64.64%, H 5.41%, N 9.06%, S 6.77%.

EXAMPLE 80

N-Benzoyldehydro-3-(2-thienyl)alanyl-L-tyrosine morpholide is obtained from A and morpholine. Melting point 120° C. (ill-defined); $[\alpha]_D^{20}$ −0.7°; yield 22% of theory.

$C_{27}H_{27}N_3O_5S$ calculated: C 64.14%, H 4.38%, N 8.32%, S 6.34%; found: C 63.92%, H 5.53%, N 8.27%, S 6.09%.

EXAMPLE 81

N-Benzoyldehydro-3-(2-thienyl)alanyl-L-tyrosine N'-benzylamide is obtained from A and benzylamine. Melting point 133° C.; $[\alpha]_D^{20}$ −69.83°; yield 68% of theory.

$C_{30}H_{27}N_3O_4S$ calculated: C 63.55%, H 5.18%, N 7.99%, S 6.10%; found: C 63.65%, H 5.25%, N 8.13%, S 6.03%.

EXAMPLE 82

N-Acetyldehydro-3-(2-thienyl)alanyl-L-tyrosine-2-dimethylaminopropylamide Melting point: 177°–179° C. (decomposition); yield: 63% of theory.

$C_{23}H_{30}N_4O_4S$ calculated: C 60.24%, H 6.59%, N 12.22%, S 6.99%; found: C 60.39%, H 6.75%, N 12.40%, S 6.89%.

EXAMPLE 83

N-Acetyldehydro-3-(2-thienyl)alanyl-L-tyrosine amide Melting point: 147° C.; yield: 79% of theory.

$C_{18}H_{19}N_3O_4S$ calculated: C 57.89%, H 5.13%, N 11.25%, S 8.59%; found: C 57.75%, H 5.20%, N 11.09%, S 8.53%.

EXAMPLE 84

N-Acetyldehydro-3-(2-thienyl)alanyl-L-tyrosine methylamide Melting point: 225° C.; yield: 50% of theory.

$C_{19}H_{21}N_3O_4S$ calculated: C 58.90%, H 5.46%, N 10.85%, S 8.27%; found: C 58.90%, H 5.47%, N 10.85%, S 8.30%.

EXAMPLE 85

N-Benzoyldehydro-3-(2-thienyl)alanyl-L-tyrosine-6-aminohexylamide Melting point: 122° C.; yield: 51.4% of theory.

$C_{29}H_{34}N_4O_4S$ calculated: C 65.14%, H 6.41%, N 10.48%, S 6.00%; found: C 65.04%, H 6.42%, N 10.45%, S 6.10%.

EXAMPLE 86

N-Benzoyldehydro-3-(2-thienyl)alanyl-L-tyrosine-4-aminobutylamide Melting point: 126° C.; yield: 70% of theory.

$C_{27}H_{30}N_4O_4S$ calculated: C 64.00%, H 5.96%, N 11.06%, S 6.32%; found: C 64.28%, H 5.98%, N 10.84%, S 6.19%.

EXAMPLE 87

N-Acetyldehydro-3-(2-thienyl)alanyl-L-tyrosinehydrazide Melting point: 240° C. (decomposition); yield: 35.3% of theory.

$C_{18}H_{20}N_4O_4S$ calculated: C 55.66%, H 5.19%, N 14.42%, S 8.25%; found: C 55.58%, H 5.28%, N 14.56%, S 8.34%.

EXAMPLE 88

N-Benzoyldehydro-3-(2-thienyl)alanyl-L-tyrosinehydrazide Melting point: 135° C.; yield: 82.2% of theory.

$C_{23}H_{22}N_4O_4S$ calculated: C 61.32%, H 4.92%, N 12.44%, S 7.11%; found: C 61.12%, H 5.02%, N 12.38%, S 7.26%.

If instead of sodium hydroxide an appropriate amine is used, the compounds which follow are formed from the corresponding 5(4H)oxazolones:

EXAMPLE 89

N-Acetyldehydrophenylalanyl-3-(2-thienyl)dehydroalanine methylamide Melting point: 226° C.; yield: 89% of theory.

$C_{19}H_{19}N_3O_3S$ calculated: C 61.77%, H 5.18%, N 11.37%, S 8.68%; found: C 61.65%, H 5.25%, N 11.6%, S 8.63%.

EXAMPLE 90

N-Acetyldehydro-3-(2-thienyl)alanyl-3-methyl-3-(2-thienyl)dehydroalanine hexylamide Melting point: 110° C.; yield: 90% of theory.

$C_{23}H_{29}N_3O_3S_2$ calculated: C 60.10%, H 6.36%, N 9.14%, S 13.96%; found: C 60.20%, H 6.56%, N 9.26%, S 13.91%.

EXAMPLE 91

N-Acetyldehydrophenylalanyl-3-(3-chlorophenyl)-dehydroalanine thiomethyl ester is obtained from 4-(3-chlorobenzylidene)-2-(1-acetamido-2-phenylvinyl)-5(4H)-oxazolone and methylmercaptan, in a pressure flask for one week. Melting point: 166°–167° C.; yield: 39% of theory.

$C_{21}H_{19}ClN_2O_3S$ calculated: C 60.79%, H 4.61%, Cl 8.54%, N 6.75%, S 7.73%; found: C 60.74%, H 4.48%, Cl 8.58%, N 6.82%, S 7.80%.

What is claimed is:

1. A dehydrooligopeptide of the following formula or its salts

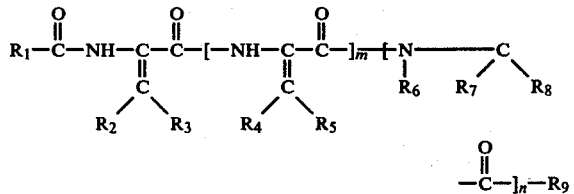

in which

R₁ is straight-chain or branched $C_1$–$C_6$-alkyl which is unsubstituted or substituted by 1 to 3 halogenatoms or $C_1$–$C_3$-alkoxy; phenyl, styryl or thienyl R₂ is hydrogen or $C_1$–$C_4$-alkyl R₃ is phenyl, naphthyl, $C_4$–$C_6$-cycloalkyl, $C_1$–$C_4$-alkyl, an unsaturated heterocyclic radical which is unsubstituted or substituted by nitro R₂ and R₃ together with the carbon atom to which they are attached represent cyclopentylidene, cyclohexylidene, cyclopentenylidene or cyclohexenylidene $R_4$ is hydrogen, methyl or ethyl $R_5$ is phenyl substituted by 1 to 3 halogen atoms or a heterocyclic group which is unsubstituted and contains 5 to 7 ring members and 1 to 2 nitrogen, oxygen or sulphur atoms $R_6$ is hydrogen $R_7$ is benzyl substituted by 1 or 2 halogen atoms or by hydroxyl or nitro; 2-methylmercaptoethyl or carboxymethyl;

$R_8$ is hydrogen $R_9$ is hydroxyl or amino, $C_1-C_{10}$-alkylamino, $C_1-C_5$-alkoxy, $C_1-C_{10}$-alkylamino further substituted by 1 to 3 amino groups or by dialkylamino and m and n are the same or different and each represents the number 0 or the number 1, provided that m and n are not simultaneously the number 0; and provided that when $R_1$ is methyl, $R_2$ is hydrogen, $R_3$ is phenyl, m represents 0, $R_6$ is hydrogen, $R_9$ is hydroxyl, $R_8$ is hydrogen and n is 1, $R_7$ does not represent the 4-hydroxybenzyl radical.

2. A dehydrooligopeptide of claim 1, in which $R_1$ is methyl, phenyl, thienyl;

$R_2$ is hydrogen or methyl;

$R_3$ is phenyl,

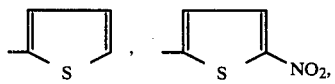

naphthyl, cyclohexyl or ethyl;

$R_2$ and $R_3$ together with the carbon atom to which they are attached stand for cyclohexglidene or cyclohexenylidene;

$R_4$ is hydrogen;

$R_5$ is

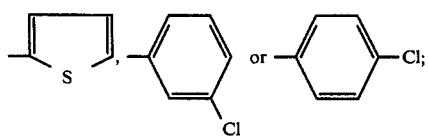

$R_6$ is hydrogen;

$R_7$ is

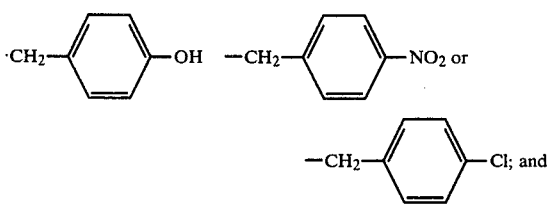

$R_9$ is OH, OCH$_3$,

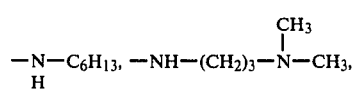

—NH—(CH$_2$)$_6$—NH$_2$ or —NH—(CH$_2$)$_4$—NH$_2$.

3. A compound of claim 1 or 2, wherein each halogen fluorine or chlorine.

4. A compound of claim 1 or 2, wherein m represents the number 0 and n represents the number 1.

5. A compound of claim 1 or 2, wherein m represents the number 1 and n represents the number 0.

6. A compound according to claim 1 or 2, which is a dehydrooligopeptide of the formula or its salts

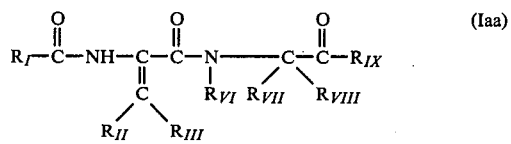

in which $R_I$ is alkyl having from one to four carbon atoms or phenyl or styryl, $R_{II}$ is a hydrogen atom, $R_{III}$ is thienyl, furyl, or cycloalkyl having five or six carbon atoms, $R_{VI}$ is a hydrogen atom, $R_{VIII}$ is the 4-hydroxybenzyl radical, 4-nitro-benzyl radical or the 4-chlorobenzyl radical, the 2-methylmercaptoethyl radical or the carboxymethyl radical, $R_{VIII}$ is a hydrogen atom, and $R_{IX}$ is hydroxyl or alkoxy having from one to four carbon atoms.

7. A compound according to claim 1 or 2 in the form of a racemic mixture.

8. A compound according to claim 1 or 2 in the form of an optically pure isomer.

9. A compound according to claim 1 or 2 in the form of a pharmaceutically acceptable salt.

10. A compound according to claim 2 which is N-Benzoyl-2-cyclohexylidenglycyl-L-tyrosine.

11. A compound according to claim 2 which is N-Benzoyldehydro-3-(2-thienyl)alanyl-L-proline.

12. A compound according to claim 2 which is N-Acetyldehydro-3-(2-thienyl)alanul-L-tyrosine.

13. A compound according to claim 2 which is N-Phenacetyldehydro-3-(2-thienyl)alanyl-L-tyrosine tert.-butyl ester.

14. A compound according to claim 2 which is N-Benzoyl-3-methyl-3-(2-thienyl)dehydroalanyl-L-tyrosine.

15. A compound according to claim 2 which is N-Benzoyldehydro-3-(2-thienyl)alanyl-L-tyrosine amide.

16. A pharmaceutical composition containing as an active ingredient an effective amount of 1 to 100 mg of a compound according to claim 1 in admixture with a solid or liquefied gaseous diluent or in admixture with a liquid diluent other than a solvent of a molecular weight less than 200 except in the presence of a surface-active agent.

17. A pharmaceutical composition according to claim 16, wherein the effective amount of active ingredient is 2 to 40 mg.

18. A pharmaceutical composition containing as an active ingredient an effective amount of a compound according to claim 16 in the form of a sterile or isotonic aqueous solution.

19. A composition according to claim 16 containing from 1 to 90% by weight of the said active ingredient.

20. A medicament in dosage unit form comprising an effective amount of 1 to 100 mg of a compound of claim 1 together with an inert pharmaceutical carrier.

21. A medicament of claim 20 in the form of ampoules.

* * * * *